United States Patent [19]

Strowe

[11] Patent Number: 5,487,395
[45] Date of Patent: Jan. 30, 1996

[54] APPARATUS FOR SUPPORTING AN ARM

[75] Inventor: Robert J. Strowe, Ramsey, N.J.

[73] Assignee: Gait Scan, Inc., Ridgewood, N.J.

[21] Appl. No.: 383,617

[22] Filed: Feb. 2, 1995

Related U.S. Application Data

[63] Continuation of Ser. No. 160,059, Nov. 30, 1993, abandoned.

[51] Int. Cl.$^6$ ....................................................... A61F 5/37
[52] U.S. Cl. .............................. 128/878; 128/846; 5/647
[58] Field of Search ................................... 128/846, 878; 5/647

[56]  References Cited

U.S. PATENT DOCUMENTS

| | | | |
|---|---|---|---|
| 1,887,022 | 11/1932 | Hoffman et al. | 128/877 |
| 2,020,262 | 11/1935 | Longfellow | 5/648 |
| 2,032,653 | 3/1936 | Ettinger | 602/39 |
| 2,198,871 | 4/1940 | Haboush | 602/39 |
| 2,393,982 | 2/1946 | Giesen | 602/39 |
| 2,732,269 | 1/1956 | Astroff | 5/646 |
| 2,871,074 | 1/1959 | Malerich, Jr. | 5/647 |
| 4,297,884 | 11/1983 | Leveque et al. | 73/579 |
| 4,562,588 | 12/1985 | Ruf | 128/882 |
| 4,646,754 | 3/1987 | Scale | 128/774 |
| 4,754,763 | 7/1988 | Doemiand | 128/739 |
| 4,799,498 | 1/1989 | Collier | 128/774 |
| 4,858,903 | 8/1989 | Lori et al. | 5/623 |

(List continued on next page.)

FOREIGN PATENT DOCUMENTS

| | | | |
|---|---|---|---|
| 2632851 | 12/1989 | France | 602/39 |
| 4022836 | 1/1992 | Germany . | |
| 1171345 | 11/1969 | United Kingdom | 128/877 |

OTHER PUBLICATIONS

C. R. Steele, Noninvasive Determination of Ulnar Stiffner from Mechanical Response—In Vivo Comparison of Stiffness and Bone Mineral Content in Humans, Journal of Biomechanical Engineering, May 1988.

Borders Peterson and Orne, "Production of Bending Strength of Long Bones for Measurements of Bending Stiffness and Bone Mineral Content", Feb. 1977, Journal of Biomechanical Eng. pp. 40–44.

Thompson, "Determination of Mechanical Properties of the Human Ulna by Means of Mechanical Impedance Tests: Experimental Results and Improved Mathematical Model," May 1976, Medical and Biological Engineering pp. 253–262.

Peterson, "In Vivo Determination of the Mechanical Properties of Bone".

Steele, Zhov, Guido, Marcus, Hendrichs, and Cheema, "Noninvasive Determination of Ulnar Stiffness from Mechanical Response,—In Vivo Comparison of Stiffness and Bone Material", Aug. 1987, Stanford University.

Steele, "Instrument for Assessment of Bone Properties", Apr. 1984, Stanford University.

Peterson, "Noninvasive Determination of Bone Stiffness," Jul. 1977, Stanford University.

*Primary Examiner*—Robert A. Hafer
*Assistant Examiner*—Michael O'Neill
*Attorney, Agent, or Firm*—Weingram & Zall

[57]  ABSTRACT

A limb supporter apparatus supports a patient's elbow on support pegs that extend under the condyles of the humerus bone for positioning the ulna bone for bone testing. The ulna extends over the humerus and is positioned close to the skin for testing. The wrist is supported in the apparatus of the present invention between two vertical support pegs to secure the wrist in a vertical position and to prevent radial movement of the wrist. This apparatus properly positions the ulna above the humerus and allows for consistent, reproducible results during testing performed on a bone. The elbow and wrist supports extend from horizontal members which are supported by vertical support members. The vertical support members are positioned on a horizontal support member which is pivotally connected to a base member. The base member may be secured to a table by attachment bolts.

16 Claims, 5 Drawing Sheets

U.S. PATENT DOCUMENTS

| | | | |
|---|---|---|---|
| 4,949,944 | 8/1990 | Groff, Sr. | 269/45 |
| 5,000,168 | 3/1991 | Lipson | 128/77 |
| 5,006,984 | 4/1991 | Steele | 364/413 |
| 5,012,820 | 5/1991 | Meyer | 128/782 |
| 5,065,770 | 11/1991 | Paltray | 128/774 |
| 5,069,229 | 12/1991 | Kurth | 128/877 |
| 5,078,152 | 1/1992 | Bond et al. | 128/774 |
| 5,136,743 | 8/1992 | Pirela-Cruz | 5/647 |
| 5,163,443 | 11/1992 | Fry-Welsh et al. | 128/782 |
| 5,228,454 | 7/1993 | Siegler | 128/782 |
| 5,228,457 | 7/1993 | Kawamura | 128/845 |
| 5,231,998 | 8/1993 | Rosen et al. | 128/878 |

APPARATUS FOR SUPPORTING AN ARM

This is a continuation of application Ser. No. 08/160,059 filed on Nov. 30, 1993 now abandoned.

BACKGROUND OF THE INVENTION

1. Field of the Invention

This invention relates to the field of testing bone qualities and more particularly to a device for supporting a limb in a fixed position for testing bone stiffness.

2. Description of the prior Art

Many efforts have been made to test bone qualities and more particularly to determine bone stiffness. These efforts culminated in U.S. Pat. No. 5,006,984 dated Apr. 9, 1991, to Steele, the entire disclosure of which is incorporated herein by reference. Steele discloses a method and apparatus for measuring physical parameters of the bone, especially the stiffness of a bone. In order for a bone to be measured in a live subject, means must be used to support the bone to be tested.

Typically, in human bone measurements are made on the ulna bone because of its proximity of the ulna bone to the skin. It is desirable to support the ulna bone as a simple beam. In the past, measurements were made by placing the wrist and elbow in "V" blocks to support the patient's limb. As so supported, testing could take place on the bone.

Several problems developed from providing such support to the patient's limb. One problem was positioning the patient's limb over the arm support. In the elbow, its difficult to provide mechanical contact to the elbow end of the ulna because of interference by the bicep muscles with the positioning of the limb. Accordingly, consistent and reproducible results were not encouraged because of variations in the support of the limb at the location of the elbow.

The previous efforts to support a limb for testing of the bone have been unable to provide the consistent and reproducible results of the present invention because of interference of the support system with the muscles or tendons of the patient.

Previous attempts in this area are as follows:

Australian Patent No. 4022-836-A (TAB A), discloses a support for an arm comprising our lower fixed rail, a hand stop and a second stop positioned against the back of the upper arm.

Domeland, U.S. Pat. No. 4,754,763, (TAB B), discloses a method of detecting bone fractures and evaluate healing the bones by applying a mechanical vibration to the bones.

Collier, U.S. Pat. No. 4,799,498, (TAB C), discloses an apparatus for detecting the resonant frequency of a bone. The testing element pierces the skin and is brought into actual contact with the bone.

U.S. Pat. No. 5,000,168, (TAB D), discloses a limb support for use by a patient for supporting a limb on a fixed surface.

Steele, U.S. Pat. No. 5,006,984, (TAB E), discloses a method and apparatus for measuring physical parameters of a bone, for example, bone density. It includes basic V blocks for catching and positioning bones and/or limbs to be tested.

Meyer, U.S. Pat. No. 5,012,820, (TAB F), discloses a device for use in measuring mechanical magnitudes during muscular contraction. The device includes a housing for holding limbs. A foot may be held in a housing having a base plate, an upper limb holder and a lower limb holder, the upper limb holder and the lower limb holder comprising straps that extend about the limb. Also included in the invention is a housing for holding a hand a thumb for examination. The thumb is supported by a U-shaped structural component.

Palfray, U.S. Pat. No. 5,065,770, (TAB G), discloses an apparatus for plotting or determining the shape or profile of a limb. The apparatus includes a plurality of splints positioned at various intervals. The splints which are deformable and can be applied tightly against a limb to match the profile thereof.

Kurth, U.S. Pat. No. 5,069,229, (TAB H), discloses an apparatus for immobilizing a knee to prevent flexing of the knee. The apparatus comprises a split, tapered, wrapping fixed around, above and below the knee.

Bond, U.S. Pat. No. 5,078,152, (TAB I), discloses a method and apparatus for diagnosis and/or treating of proprioceptor feedback capabilities in a human muscle and joint system. The apparatus includes a passive resistance system having a lever arm assembly with a patient attachment cuff mounted thereto. This assembly allows the patient to move a limb radially during an exercise motion.

Pierela-Cruz, U.S. Pat. No. 5,136,743, (TAB J), discloses a distill radioulnar joint stress platform comprising a pair of upright blocks mounted to the platform in a spaced relationship to permit a wrist to be positioned therebetween, a post on the platform near one end thereof for gripping by the subject, and a pair of stabilizing brackets adjustably mounted to each block for contacting the side of the fore arm to hold the fore arm in a preselected position for examination.

Fry-Welsh, U.S. Pat. No. 5,163,443, (TAB K), discloses a method and apparatus for measuring hand, wrist and fore arm strength. The apparatus comprises a frame supporting a harness in the center thereof by means of a plurality of coupling links. Also included is a fore arm support for the subject to rest its fore arm Rosen et al., U.S. Pat. No. 5,231,998, (TAB L), discloses an apparatus for steadying limb motion for limiting involuntary movement of the limb. The device includes a limb coupler cuff assembly comprising a U-shaped support coupled to a limb coupler trough or cuff in which the fore arm is held.

Siegler, U.S. Pat. No. 5,228,454, (TAB M), discloses an apparatus and method for determining load-displacement and flexibility characteristics of a joint. The apparatus includes first and second frames for receiving first and second ends of a limb. A pivot assembly is provided between the first and second frames to allow the first frame to pivot with respect to the second frame. Also included are straps for securing the limb in position between the first and second frames.

Kawamura, U.S. Pat. No. 5,228,457, (TAB N), discloses a protector for a heartbeat-synchronous pulse wave detecting probe used in the limb of a patient. The protector comprises a flat portion for positioning underneath the limb and a shield portion extending from the flat portion to protect the detecting probe from contacting any medical staff.

U.S. Pat. No. 4,297,884 to Leveque et al. discloses a method and apparatus for testing the elastic characteristics of an object. The sample to be tested is held at one end between jaws and a hooking element.

"PREDICTION OF BENDING STRENGTH OF LONG BONES FOR MEASUREMENTS OF BENDING STIFFNESS AND BONE MINERAL "CONTENT" by Borders, Peterson and Orne discloses three point and four point bending testing of bones. The support system is simple.

DETERMINATION OF MECHANICAL PROPERTIES OF THE HUMAN ULNA BY MEANS OF MECHANICAL IMPEDANCE TEST: EXPERIMENTAL RESULTS AND IMPROVED MATHEMATICAL MODEL by Thompson, Orne and Young discloses an apparatus including an electromagnetic shaker and a simple two point support for the ulna. The support at the wrist includes a strap that extends over the top of the wrist. Additionally, the device could include small plaster pads caste to conform to bony prominences at both the wrist and the elbow.

IN VIVO DETERMINATION OF THE MECHANICAL PROPERTIES OF BONE by Peterson discloses in vivo tests on a monkey wherein the fore arm rests on two supports in a manner such that the ulna can be modeled as a simply supported beam. Additional experiments were conducted on a foam foundation in a manner so that the ulna can be modeled as a beam on an elastic foundation. The subject was pushed down gently through the humerus to constrain the olecranon end of the ulna for moving. A small plastic pad made to fit the contour of the bone at both the elbow and the wrist were placed on top of each support.

NONINVASIVE DETERMINATION OF ULNA STIFFNESS FROM MECHANICAL RESPONSE-IN VIVO COMPARISON OF STIFFNESS AND BONE MINERAL by Steele, Zhou, Guido, Marcus, Heinrichs and Cheema discloses a test configuration wherein the ulna is simply supported at the wrist and elbow.

INSTRUMENT FOR ASSESSMENT OF BONE PROPERTIES by Steele discloses a test where the ulna is simply supported at the elbow and wrist. Additionally, a system showing utilizing vertical positioning of the bone under tests is disclosed.

NONINVASIVE DETERMINATION OF BONE STIFFNESS by Peterson discloses simply supporting the ulna at the elbow and the wrist. The support for the elbow was placed directly under the greater sigmoid cavity. Plaster was molded under the elbow and at the wrist so that the ulna was restrained against even small lateral motion at the supports. And further, with respect to testing a monkey arm, a two kilogram weight was placed on top of the humerus to constrain the ulna. The experiment was repeated with duct seal substituted for the plaster pads which held the ulna in position at each end. The duct seal was not only more comfortable than the plaster pads but it saved time in setting up the experiment.

Steele, U.S. Pat. No. 4,646,754, discloses a method and apparatus for inducing vibrations to elements of the human body and detecting the responses for determining mechanical characteristics of the elements. The apparatus includes a vibrator plate configured to contact the skin surface.

None of these previous attempts, taken either alone or in combination, teach or suggest the structure and the advantages and benefits of Applicant's present invention.

OBJECTS AND SUMMARY OF THE INVENTION

The apparatus of the present invention overcomes the deficiencies associated with supporting a limb with "V" blocks. The apparatus of the present invention supports the patient's elbow on support pegs that extend under the condyles of the humerus bone. The support pegs extend from behind the patient's elbow. This allows for good mechanical support of the ulna bone which is interconnected with the humerus bone at the elbow and extends over the humerus bone. When a patient's arm is positioned in the apparatus of the present invention, the ulna extends over the humerus and is positioned close to the skin in a position desirable for testing. The wrist is supported in the apparatus of the present invention between two vertical support pegs to secure the wrist in a vertical position and to prevent radial movement of the wrist. Again, this works to properly position the ulna above the humerus and allows for consistent, reproducible results during testing performed on a bone.

Accordingly, it is an object of the limb supporter apparatus of the present invention to provide an apparatus for supporting a limb for testing a bone.

It is a further object of the limb supporter apparatus of the present invention to support the ulna bone for testing.

It is a still further object of the limb supporter apparatus of the present invention to provide mechanical support of a limb at the ends of the limb.

It is another object of the limb supporter apparatus of the present invention to support an arm with support pegs positioned below the condyles of the humerus.

It is yet another object of the limb supporter apparatus of the present invention to support a arm with vertical support pegs positioned along the wrist.

It is still a further object of the limb supporter apparatus of the present invention to provide results that can be reproduced.

It is even another object of the limb supporter apparatus of the present invention which will position a patient's arm consistently in the same position.

It is an additional object of the limb supporter apparatus of the present invention to position both the right and left arms of a patient for testing.

It is yet an additional object of the limb supporter apparatus of the present invention to be easily adjusted to the patient's size.

It is still an additional object of the limb supporter apparatus of the present invention to stabilize a limb for other applications such as performing tests on a bone that is covered by a cast.

It is a further object of the limb supporter apparatus of the present invention to have other applications such as stabilizing a limb for CT or MRI testing.

It is even a further object of the limb supporter apparatus of the present invention to stabilize a limb for surgical procedures.

These as well as further objects and advantages of this invention will become apparent to those skilled in the art from a review of the accompanying detailed description of the preferred embodiment, reference being made to the accompanying drawings.

BRIEF DESCRIPTION OF THE DRAWINGS

The invention will be described with reference to the accompanying drawings in which.

DETAILED DESCRIPTION

As shown in FIGS. 1–4, the limb supporter apparatus of the present invention is generally indicated at 10. The limb supporter includes a base, generally indicated at 20 for attachment to a table 11, or other support surface, having slots 12 formed therein. The base 20 includes a horizontal base member 21 that rests on the table 11, the lower surface 23 of the horizontal base member 21 contacting the table 22.

The base 20 may be secured to the table 11 by means of attachment bolts 26 which are received by threaded apertures 24 in the horizontal base member 21. Attachment bolts 26 include bolt handles 28 for manipulating the attachment bolts 26. The bolt handles 28 include attachment surfaces 30 for contacting the underside of the table 11 for securing the horizontal base member 21 to the table or support surface 11. Note that there may be two or more attachment bolts for securing the horizontal base member 21 to the table 11.

The procedure for securing the horizontal base member 21 to the table 11 includes loosening the attachment bolts 26, sliding the horizontal base member 21 onto the table or support surface 11, the attachment bolts 26 extending into the slots 12. Then, the attachment bolts 26 are tightened by means of the bolt handles 28 to secure the horizontal base 21 to the table or support surface 11. It should be noted that other means of supporting the limb supporter 10 may be utilized including permanent attachment to the horizontal base member 21 to a table 11 or moveable platform, or by clamping the base member 21 to the table 11. Other means of tightening the attachment bolts may be utilized, for example, nuts could be positioned on the attachment bolts The horizontal base member 21 includes an upper surface 23 which supports a pivot mount 34 and an adjuster mount 40. Typically, the pivot mount 34 is positioned at an end of the horizontal base member 21 and the adjuster mount 40 is positioned at some intermediate point of the horizontal base member 21. The adjuster mount 40 and the pivot mount 34 are connected to the horizontal base member 21 in any manner known in the art.

Extending from the adjuster mount 40 is adjuster mount channel 42 which interconnects with adjuster bolt receiving channel 44 by means of adjuster pivot connection means 46. The adjuster bolt receiving channel 44 includes an aperture for receiving adjuster bolt 50. The adjuster mount channel 40 and adjuster bolt receiving channel 44 are interconnected by adjuster pivot connection means 46 which allows the adjuster bolt receiving channel 44 to coact with the adjuster mount channel 42 to permit the adjuster bolt receiving channel 44 to pivot with respect to the adjuster mount channel 42. Again, this pivot connection is not limited by the structure described herein and shown in the figures, but can be provided in any manner known in the art.

The pivot mount 34 is interconnected with pivot support channel 62 by pivot connector 36 to allow for pivoting of the pivot support channel 62 with respect to the pivot mount 34 and the horizontal base member 21. Mounted to the pivot support channel 62 is first end of horizontal member 60.

Horizontal member 60 is also interconnected with the horizontal base member 21 at an intermediate point of both the horizontal member 60 and the horizontal base member 21, by means of adjuster bolt 50. As such, the horizontal member 60 has adjuster mount 64 mounted to it at an intermediate point of the horizontal member 60. The adjuster mount 64 includes adjuster mount aperture 66 for permitting the adjuster bolt 50 to pass therethrough. As such, the adjuster bolt 50 interconnects the horizontal member 60 by way of adjuster mount 64 with the horizontal base member 21 by way of adjuster bolt receiving channel 44 and adjuster mount channel 42. The adjuster bolt extends through the adjuster mount aperture 66 to the adjuster bolt receiving channel 44.

Adjuster bolt 50 includes an adjuster bolt handle 52 and an adjuster bolt contact surface 54 on the underside of the adjuster bolt handle. As such, the adjuster bolt 50 may be rotated by means of the adjuster bolt handle 52. Such rotation causes the horizontal member 60 to move vertically with respect to the horizontal base member 21, the horizontal member 60 pivoting about the pivot connector 36 to allow for restrained adjustable rotational motion of the horizontal member 60 with respect to the horizontal base member 21 in the direction of arrow A in FIG. 2.

Horizontal member 60 includes horizontal extension member 68 which extends telescopically from horizontal member aperture 69 located at second end of the horizontal member 60. Additionally, horizontal lock bolts 70 extends through an aperture facing the horizontal member aperture 69 and contacts the horizontal extension member 68 within the horizontal member aperture 69 for securing the horizontal extension member 68 with respect to the horizontal member 60. As such, the effective length of the horizontal member 60 may be adjusted by telescopically extending or retracting the horizontal extension member 68 from the horizontal member 60 along the direction of arrow B in FIG. 3. Such positioning may be fixed by manipulating the horizontal lock bolt 70. Additionally, adjustability of the horizontal member 60 may be achieved by other means known in the art.

Extending up from the horizontal member 60 are vertical wrist support member 80 and vertical elbow support member 90. These vertical support members 80 and 90 are positioned at the first and second ends of the horizontal member 60, the vertical wrist support member 80 mounted on and extending from the horizontal extension member 68, and the vertical elbow support member 90 mounted on and extending from the first end of the horizontal member 60 proximate to the pivot support channel 62. As such, the distance between the vertical wrist support member 80 and the vertical elbow support member 90 may be adjusted by telescopically extending or retracting the horizontal extension member 68 from the horizontal member 60. Again, the distance between the vertical elbow support member 90 and the wrist support member 80 may be adjusted by other means, for example, the wrist support member 80 could be mounted on a sleeve slidable along the horizontal member 60, or on a pin received by a slot in the horizontal member 60.

Formed at the top end of the vertical wrist and elbow support members 80 and 90 are vertical wrist and elbow support necks 81 and 91, respectively, which receive horizontal wrist and elbow support member 82 and 92 respectively. The horizontal wrist and elbow support members 82 and 92 including horizontal wrist and elbow support apertures 83 and 93, respectively, which receive the vertical wrist and elbow support necks 81 and 91. The horizontal wrist and elbow support members 82 and 92 are removably interconnected with the vertical wrist and elbow support members 80 and 90 to permit repositioning of the horizontal wrist and elbow support members 82 and 92 for alternatively testing the left and right limbs of a patient.

The horizontal wrist and elbow support members 82 and 92 include threaded apertures for accepting wrist and elbow lock bolts 84 and 94 respectively for locking the position of the horizontal wrist and elbow support members 82 and 92 with respect to the vertical wrist and elbow support members 80 and 90. The apertures extend through faces of horizontal wrist and elbow support members 80 and 90 at the horizontal wrist and elbow support apertures 83 and 93 to permit wrist and elbow lock bolts 84 and 94 to contact the vertical wrist and elbow support necks 81 and 91 to hold the positions of the horizontal wrist and elbow support members 82 and 92.

Horizontal wrist support member 82 includes horizontal wrist extension member 85 which telescopically extends from an aperture within the horizontal support member 82. The horizontal support member 82 also includes a second threaded aperture for receiving a horizontal wrist extension lock bolt 86 for securing the horizontal wrist extension member 85 with respect to the horizontal wrist support member 82.

Positioned to extend from the horizontal wrist extension member 85, in a vertical direction, is wrist support peg 88. Positioned at the end of the horizontal wrist member 82 is another wrist support peg 88. By varying the distance that the horizontal wrist extension member 85 is extended, in the direction of arrow C in FIG. 3, with respect to the horizontal support member 82, the distance between the wrist support pegs 88 may be increased or decreased. The wrist support pegs extend vertically from the horizontal wrist extension and horizontal wrist support members 85 and 82. As previously set forth with respect to the horizontal member, adjustability of the horizontal elbow and wrist support member 92 and 82 could be achieved in any manner known in the art, including a sleeve extending about and slidable along the horizontal elbow and wrist members 92 and 82 or a pin riding in a slot in the members 92 and 82.

Horizontal elbow support member 92 includes horizontal elbow extension member 95 which telescopically extends from an aperture within the horizontal support member 92. The horizontal support member 92 also includes an aperture for receiving a horizontal elbow extension lock bolt 96 for securing the horizontal elbow extension member 95 with respect to the horizontal elbow support member 92.

Positioned to extend from the horizontal elbow extension member 95, in a horizontal direction, is a elbow support peg 98. Positioned at the end of the horizontal elbow member 92 is another elbow support peg 98. By varying the distance that the horizontal elbow extension member 95 is extended with respect to the horizontal support member 92, the distance between the wrist support pegs 98 may be increased or decreased. The elbow support pegs 98 extend horizontally from the horizontal elbow extension and horizontal wrist support members 95 and 92.

Figure 1:
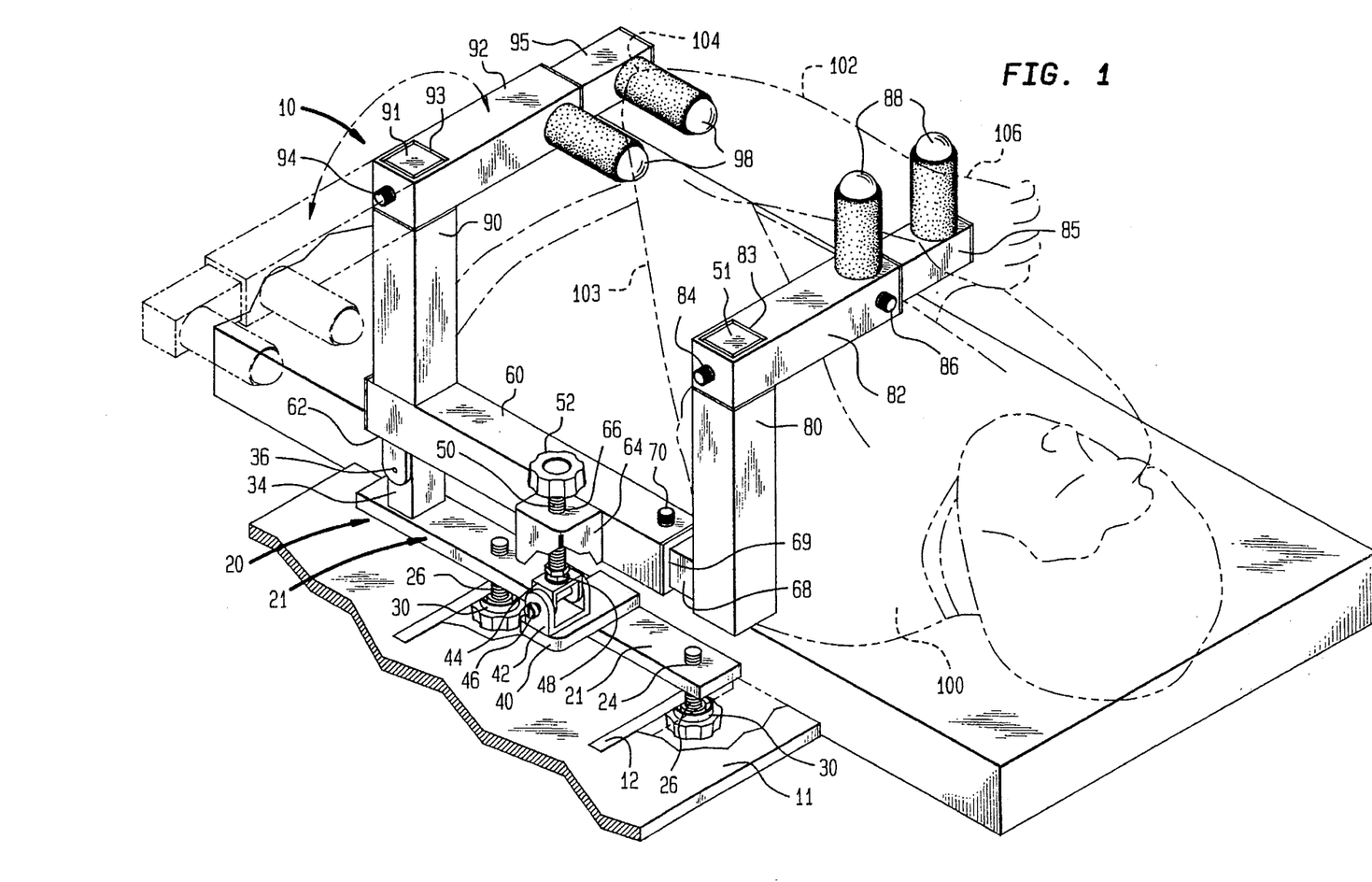
FIG. 1 is a perspective view of the limb supporter apparatus of the present invention showing a patient in phantom lines.
Figure 2:
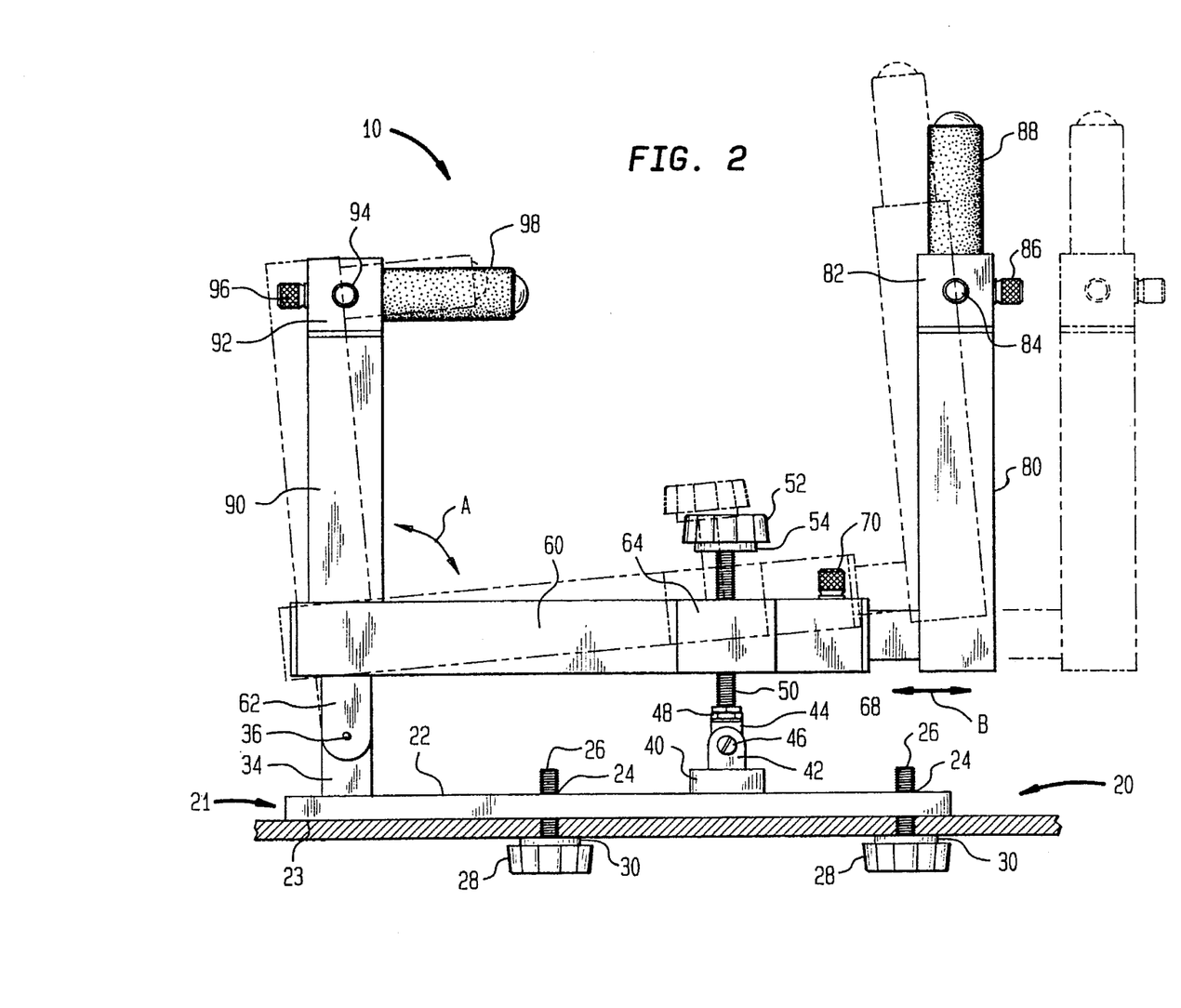
FIG. 2 is a side plan view of the apparatus of FIG. 1 showing some of the adjustments permitted.
Figure 3:
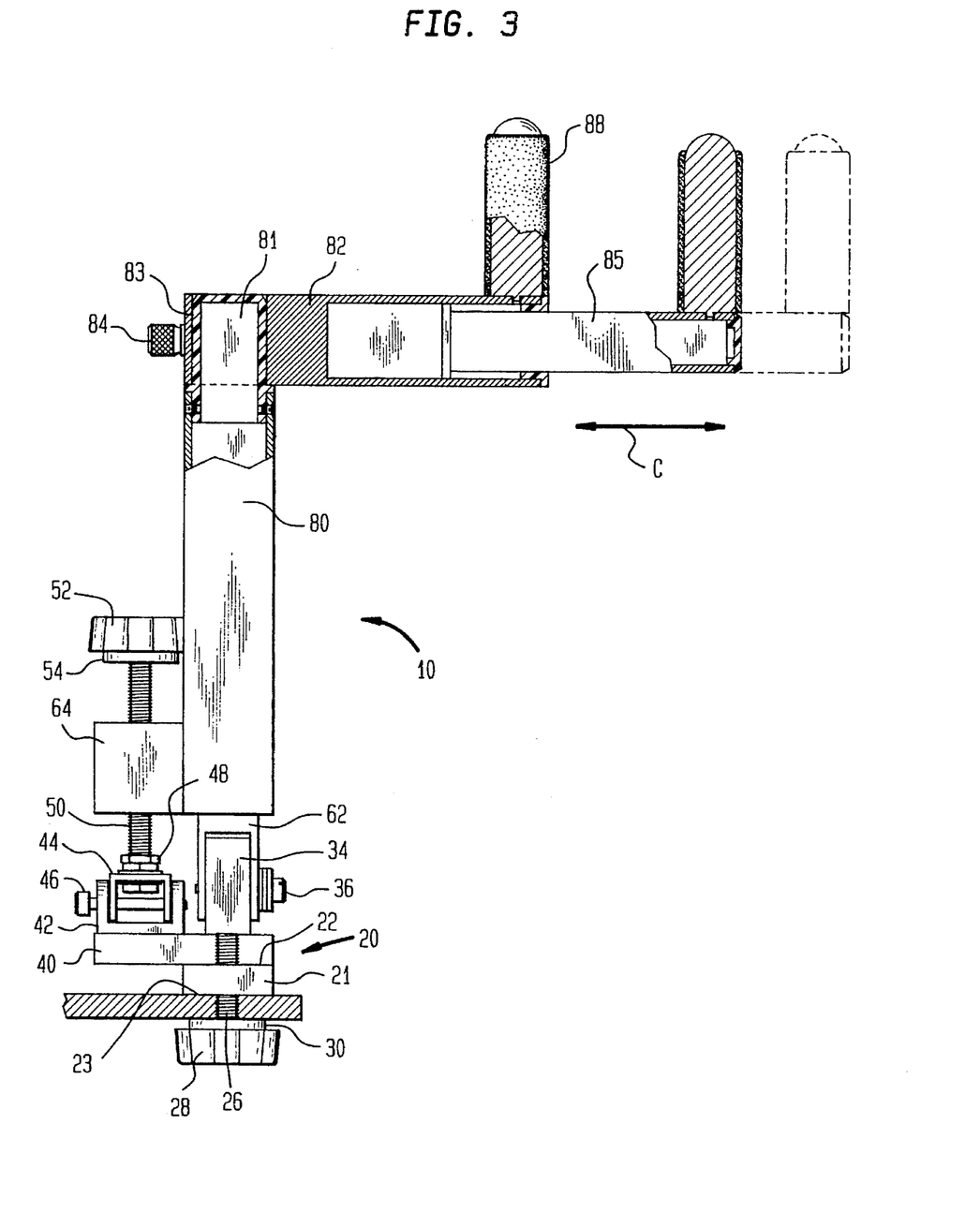
FIG. 3 is a front plan view of the apparatus of FIG. 1 showing some of the adjustments permitted.
Figure 5:
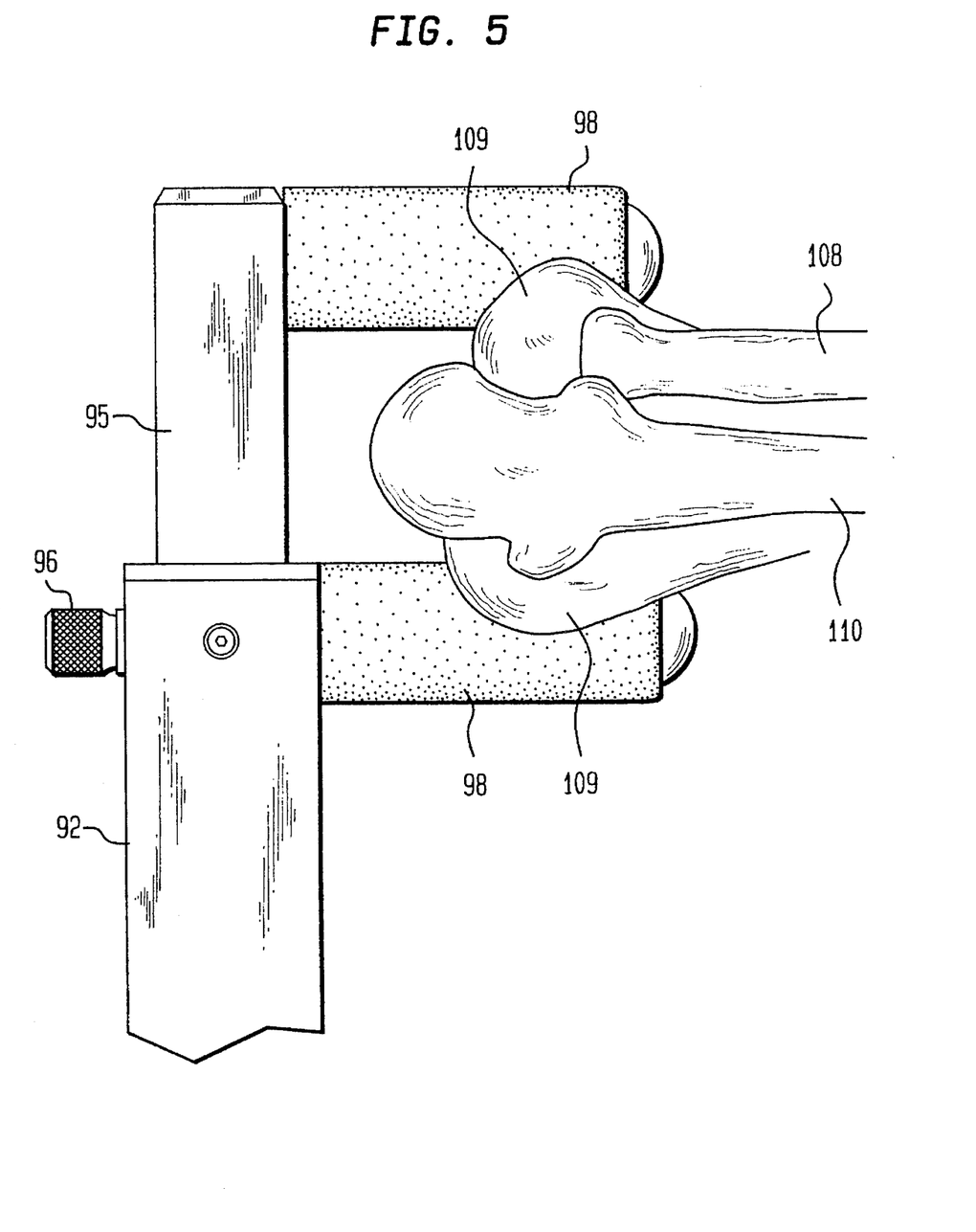
FIG. 5 is a enlarged plan view of the elbow support of the apparatus shown in FIG. 1 with the patient's humerus and ulna bones positioned thereon.

In operation, as shown in FIG. 1, it is desirable for a patient 100 to lay down on his or her back and raise his or her arm up from the body for positioning in the limb supporter 10. The patient's upper arm 103 will be raised up to be perpendicular to the plane of the patient's body or even past perpendicular to the plane of the body. The elbow 104 is positioned on the elbow pegs 98 and the wrist 106 is positioned between the wrist pegs 88. Specifically, the elbow is placed above the elbow support pegs 98 and that the elbow support pegs 98 are moved together so that the elbow support pegs 98 extend below the condyles of the humerus to support the elbow. Importantly, the elbow support pegs 98 extend and support the patient's elbow from behind the patient's elbow and thus don't contact or interact with the patient's biceps or other muscles and tendons that interfered with supporting the patients limb in the past. As shown in detail in FIG. 5, pegs 98 are positioned below the condyles 109 of the humerus 108 support the patient's elbow.

A patient's wrist is placed vertically between wrist support pegs 88, the wrist support pegs 88 being adjusted by manipulating the horizontal wrist extension member 85 with respect to the horizontal wrist support member 82 to position the wrist support pegs 88 along the sides of the wrist 106 to maintain the wrist in a vertical position. Horizontal wrist extension lock bolt 86 is used to secure the positioning of the wrist support pegs 88.

As such, the patient's arm is supported in the limb supporter apparatus of the present invention so that the ulna bone is positioned over the humerus bone and close to the skin to expose the ulna for testing. The arm is supported at one end by the condyles of the humerus and at the other end at the wrist.

Additionally, it should be noted that the angle at which the ulna is supported can be adjusted by manipulating adjuster bolt 50 to pivot horizontal member 60 about pivot connector 36. This allows one to adjust the limb supporter 10 to position and to provide the ulna bone at a proper vertical location for being met by a testing apparatus such as the probe disclosed in U.S. Pat. No. 5,006,984 to Steele.

Figure 4:
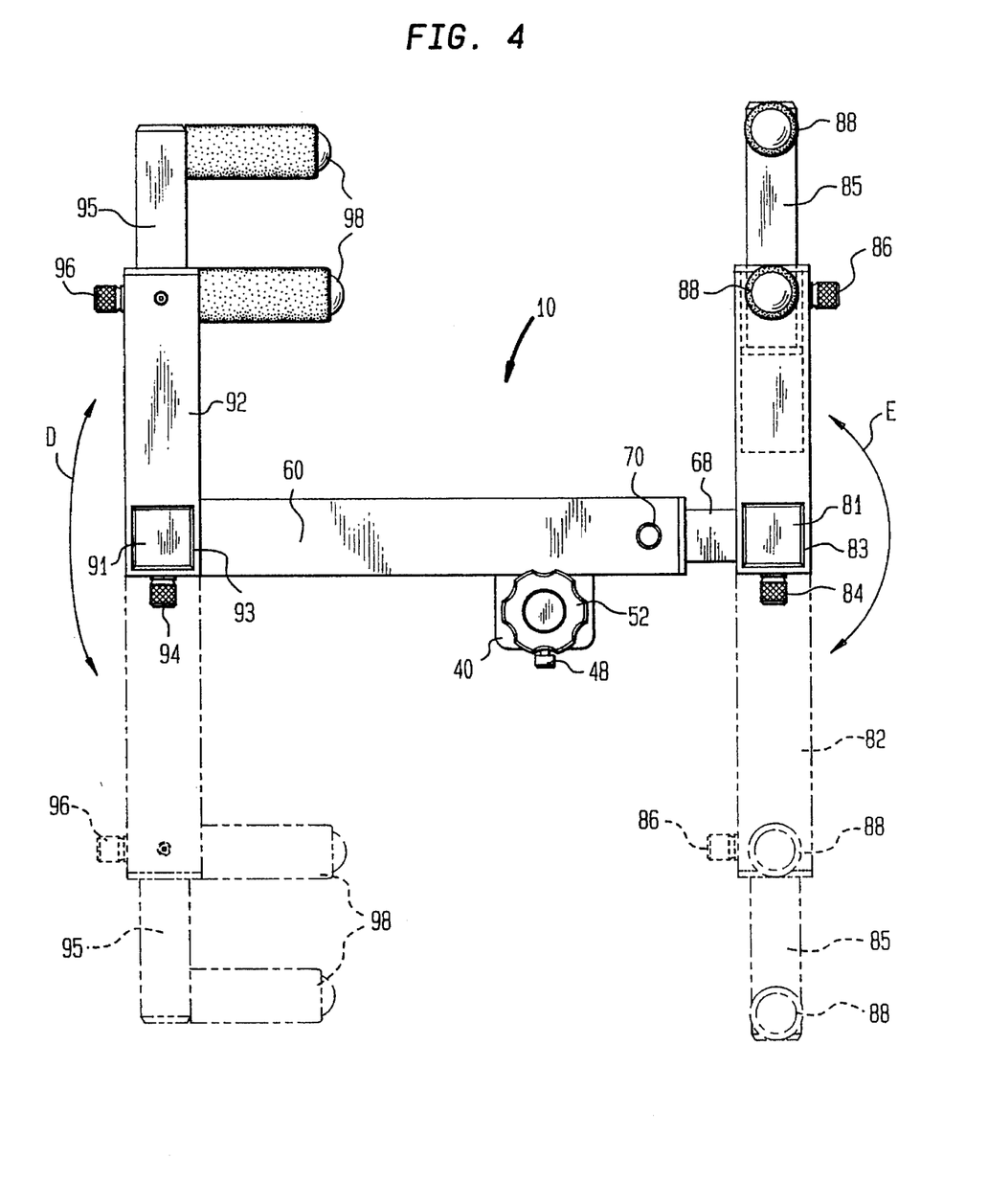
FIG. 4 is a top plan view of the apparatus of FIG. 1 showing some of the adjustments permitted.

Importantly, the limb supporter 10 of the present invention can be utilized on both limbs of a patient. However, it is important that the elbow is always placed at the end of the device having the pivot connector 36 so that the device can be pivoted to properly position the arm. In order to accomplish the use of the same device for use both of the patient's arms, the horizontal wrist support member 8Z and the horizontal elbow support members 92 are adjustable. In order to change the elbow support members 82, as shown in FIGS. 1 and 4, from the shown position to the position in phantom lines, the elbow lock bolt 94 is loosened to allow the horizontal elbow support member 92 to be removed from the vertical support neck 91. Then the horizontal elbow support member is flipped over, along the line of arrow D, to the phantom position. In this position, the horizontal elbow support aperture 93 again receives the vertical support neck 81, but from the opposite direction. The elbow lock bolt 94 can then be manipulated to secure the horizontal elbow support member 92 to the vertical support member 90.

Likewise, FIGS. 1 and 4 show that the horizontal wrist support member 82 can be removed from the vertical wrist support member, rotated 180°, along arrow E, and reattached to the vertical wrist support member 92 to change the apparatus from a configuration for testing the patient's left arm to testing the patient's right arm.

It should be noted that the members shown in the figures discussed herein may be constructed in any suitable manner. As shown in the figures, the members are generally square in cross-section, comprising four walls of approximately equal width arranged in a square. As such, the centers are hollow.

Likewise, it should be pointed out that the various members comprising the present invention may be interconnected with the various other members to which they are attached by any means known in the art, including by welding.

Additionally, it should be pointed out that the support pegs 88 and 98 may be formed in any suitable manner. For example, the support pegs 88 and 98 may comprise metal pegs threadibly attachable to the horizontal wrist and elbow support members 82 and 92. Additionally, the pegs may include a foam or rubber covering to provide increased resistance against slipping of the patient's arm and to provide comfort to the patient when positioning a limb to be supported. The pegs may comprise cylindrical shafts, preferably with rounded exposed ends. Also, the pegs could have varying profiles including a square profile, a flat strip profile, or an arced or curved profile. Again., any other configurations of the pegs in order to provide better positioning or greater comfort to the patient can be considered within the scope of this invention.

Having thus described my invention in detail, it is to be understood that the foregoing description is not intended to limit the spirit and scope thereof. What is desired to be protected by Letters Patent as set forth in the appended claims.

What is claimed is:

1. An apparatus for supporting an arm comprising:

base means;

first and second vertical support means extending from the base means;

elbow support means attached to the first vertical support means for supporting an elbow, the elbow support means comprising:

a pair of members spaced to support an elbow by the condyles of the humerus;

the pair of members extending generally horizontal with respect to the base means;

the pair of members slideably moveable with respect to each other to vary the space between the pair of members for supporting various sized elbows;

the members positioned generally parallel to each other and maintained in said generally parallel relationship when moved with respect to one another; and wrist support means attached to the second vertical support means for supporting a wrist.

2. The apparatus of claim 1 wherein the members comprising the elbow support means are cylindrical.

3. The apparatus of claim 2 wherein the members comprising the elbow support means are covered by a cushioning means.

4. The apparatus of claim 3 wherein the wrist support means comprises a pair of members having a space therebetween, the members supporting a wrist therebetween.

5. The apparatus of claim 4 wherein the members comprising the wrist support means are parallel.

6. The apparatus of claim 5 wherein the members comprising the wrist support means are cylindrical.

7. An apparatus for supporting a limb comprising:

a base having first and second ends;

attachment means for attaching the base to a base support surface;

a horizontal support member having first and second ends, the support member pivotally connected to the base at the first ends thereof;

a first vertical support having first and second ends, the first vertical support interconnected with the horizontal support member at the first ends thereof;

an elbow support member interconnected with the first vertical support at the second end of the first vertical support;

a second vertical support having first and second ends, the second vertical support attached to the second end of the horizontal support member;

a wrist support member attached to the second end of the second vertical support;

the elbow support having a first end and a second end, the second end having a support peg mounted thereon, and a receiving means for receiving an elbow extension member, the elbow extension member having a support peg mounted thereon; and the wrist support having a first end and a second end, the second end having a support peg mounted thereon and a receiving means for receiving a wrist extension member, the wrist extension member having a support peg mounted thereon.

8. The apparatus of claim 7 wherein the attachment means comprises:

slots formed in a base support surface;

threaded apertures provided in the base;

attachment bolts to threadibly engage the threaded apertures in base;

the attachment bolts having engagement surfaces;

the bolts extending through slots formed in the base support surface;

the engaging surface of the bolts contacting the base support surface; and the base contacting the base support surface to secure the base to the base support surface.

9. The apparatus of claim 8 wherein the pivot connection between the horizontal support member and the base comprises a pivot mount interconnected with the base member and a channel means interconnected with the horizontal support member, the channel means including side walls extending about the pivot mount, and connecting means for pivotally connecting the pivot channel and the pivot mount.

10. The apparatus of claim 9 further comprising adjustment means interconnecting the base member and the horizontal support member at a position intermediate the ends of the base and horizontal support member for adjusting the vertical distance between the base member and the horizontal support member.

11. An apparatus for supporting a limb comprising:

base means;

horizontal support means pivotally connected to the base means;

first and second vertical support means extending from the horizontal support means;

elbow support means attached to the first vertical support means for supporting an elbow;

the elbow support means comprising a first elbow support peg extending horizontally from the elbow support means and a second elbow support peg positioned parallel to the first peg, the elbow support peg spaced to support an elbow below the condyles of the humerus;

the elbow support means further including an elbow support extension means extending from an aperture in an end of the elbow support means, the elbow support extension means carrying one elbow support peg and the elbow support means supporting the other elbow support peg; and wrist support means attached to the second vertical support means for supporting a wrist;

the wrist support means including two wrist support pegs extending vertically upward from the wrist support means, the wrist support pegs spaced to retain a wrist therebetween.

12. The apparatus of claim 4 wherein the wrist support means includes a wrist support extension means extending from an aperture in an end of the wrist support means, the wrist support extension means carrying one of the wrist support pegs and the wrist support means carrying the other wrist support peg.

13. The apparatus of claim 5 wherein the members comprising the wrist support means are covered by a cushioning means.

14. The apparatus of claim 11 wherein the members comprising the elbow support means are moveable with respect to each other.

15. The apparatus of claim 14 wherein the members comprising the wrist support means are moveable with respect to each other.

16. The apparatus of claim 15 wherein the first and second vertical support means are moveable with respect to each other.

* * * * *